US00PP08157P

United States Patent [19]

Austin

[11] Patent Number: Plant 8,157

[45] Date of Patent: Feb. 23, 1993

[54] ROSE PLANT—'AUSMIT'

[75] Inventor: David C. H. Austin, Albrighton, England

[73] Assignee: David Austin Roses, Albrighton, England

[21] Appl. No.: 623,308

[22] Filed: Dec. 6, 1990

[51] Int. Cl.[5] ..... A01H 5/00

[52] U.S. Cl. ..... Plt./1

[58] Field of Search ..... Plt./1, 21

*Primary Examiner*—Howard J. Locker

*Attorney, Agent, or Firm*—Ladas & Parry

[57] ABSTRACT

A new variety of rose plant of the shrub class distinctive in its character by its fully double, pale, creamy apricot flowers with abundant continual blooming, and the unusual shaping of the flowers.

1 Drawing Sheet

BACKGROUND OF THE INVENTION

The present invention relates to a new and distinct variety of shrub roses, said new variety originating as a single seedling resulting from a definite effort to produce an improvement in this class of rose.

BRIEF SUMMARY OF THE INVENTION

Primary features of this new variety which connote a distinctive advance over existing types are the vigorous abundant and continual blooming that occurs for 5 months taken with the perfection of the fully double flowers of an old-fashioned shape, more particularly apparent in the accompanying illustration of a specimen thereof. It is also noted that the unusual and pleasing petal colouration intensified in colour darkness with blossom, age and exposure.

BRIEF DESCRIPTION OF THE DRAWING

The accompanying illustration shows typical cultivar flowers of this new cultivar in various stages of development, depicted in color as nearly true as is possible to make the same in color illustrations of this character.

DETAILED BOTANICAL DESCRIPTION

The following is a detailed description of the new variety, color terminology being in accordance with the "Methuen Handbook of Colour" published by Eyre Methuen Ltd (1963).

Variety denomination (in accordance with the UPOV Convention): Ausmit.

*Cultivar trade name.*—St. Cecilia.

*Type.*—Hardy, outdoor, bush, seedling, for cut flowers and garden decoration.

*Class.*—Shrub.

Propagation. The variety holds its distinguishing characteristics through succeeding propagations by budding.

Asexual reproduction of the new cultivar by budding has taken place at a nursery in Albrighton, Nr. Wolverhampton, England and it was derived as follows:

Female parent (seed parent) Unknown seedling.

Male parent (pollen parent): Unknown seedling.

The operation of the artificial pollination is therefore expressed by the following unknown seedling×unknown seedling.

The following observations are made of specimens grown outdoors in England.

PLANT DESCRIPTION

Plant

*Height.*—100 cm.

*Habit.*—Strong, bushy.

Branches:

*Young stems.*—Color: 29D7 Greyish green. Texture: Smooth. Thorns: 2–5 per node, 1–3 mm long 10C7 brownish red at base fading to greyish yellow 1B4 with numerous red glandular hairs.

*Old stem.*—Color: 30E8 Parrot green. Texture: Rough. Thorns: Numerous red glandular hairs and numerous thorns 1–7 mm 11D8 claret.

LEAVES

Stipules:

*Length.*—20–25 mm.

*Width.*—6–8 mm.

*Angle of wingtips to petiole.*—45°.

*Color.*—1B5.

*Margins.*—Linear or slightly convex, finely toothed with red tipped glandular hairs. Mid rib greyish red 10D5.

*Shape.*—Medium width.

Petiole:

*General description.*—Length: 80–95 mm. Upperside color: 30E8 Parrot green, groove margins and nodes tinged with brownish violet 11D7. Groove/hairs/thorns: Groove sparsely lined with red glandular hairs. Underside: 2B4 greyish yellow with pale pink tinge 10A2. Hair/thorns: Occasional red glandular hairs.

Leaflets:

Number.—3, 5, most often 7.

*Shape.*—Ovoid with rounded base and cuspidate apex.

*Serration.*—Serrate.

*Texture.*—Leathery dull.

General effect of foliage: Medium density and dull.

Color

*Young foliage.*—Upperside: 30E8 deep green with violet brown 8D5 mid rib and margins. Underside: 29D6 greyish green with 11E5 violet brown blush and margins.

*Adult foliage.*—Upperside: 28F8 dark green. Underside: 28E6 greyish green.

INFLORESCENCE

Number of flowers per stem: 2–5 mostly 4.
Peduncle:
Length.—40–60 mm.
*Color.*—30D8 deep green.
*Thorns/hairs.*—Sparse red tipped glandular hairs.
Sepals:
*Upperside color.*—29D8 deep green with faint pinkish brown blush on outer sepals.
*Outer margins.*—With long enisform protrusions of red tipped glandular hairs.
*Inner margins.*—Densely tomentose.
*Underside color.*—29D6 medium green.
*Texture.*—Outer sepals slightly ridged and dented.
*Sepal length.*—30 mm.
Bud shape.—Round with long cuspidate tip.
*Length.*—33 mm.
*Max. width.*—13 mm.
*Color when opening.*—11C7 Fraise fading to 8A3 shell pink.
Flower shape.—Rounded sides, flat top and base.
*Diameter.*—70 mm.
*Color when opening.*—Upperside: Outer petals: 3A4 pastel yellow at base changing 9A2 pale pinkish white. Inner petals: Basal tip 3A6 yellow fading through 3A4 pastel yellow to 5A2 orange white. Underside: Outer petals: Basal tip 3A4 pastel yellow fading through 5A3 pale orange to pale 9A2 pinkish white. Inner petals: Basal tip 3A5 light yellow fading through A4 pastel yellow to 8A2 reddish white.
*Color when blooming.*—Upperside and most of petal: Basal tip 2A6 yellow fading through 2A3 pale yellow to very pale 9A2 pinkish white. Underside and most of petal: Basal tip 2A6 yellow fading through 2A3 pale yellow to 9A2 pinkish white.
*Coloring when finished blooming.*—Upperside: Outer petals: Basal tip 2A4 pastel yellow fading to very, very pale 10A2 pinkish color. Inner petals: White (almost white). Underside: Outer petals: As for outer petal but a slightly darker 10A2 pinkish color. Inner petals: White (almost white).

Length of season of blooming at location of production: from June to October.
Fragrance: Good, myrrhy.
Lasting quality: Average.
*Range of days on plant.*—8–12 days.
*Range of days as cut flowers.*—7–9 days.
Petals
*Shape.*—outside: Rounded margins, smooth and slightly irregular at top. The base is shouldered and cuneate with the petal deeply cupped. Middle and inside: Oblong, top broad, round, margin irregular. Base acute. Petal slightly cupped.
*Texture.*—Silky.
*Number.*—95–100 average where inner 6–8 petals resemble stamens grown together to in turn resemble petals petaloid.
*Cleaning.*—Good drops its petals quickly leaving a tidy looking rose.
Stamens:
*Number.*—About 110.
*Anthers.*—Normal, bright golden yellow 3A6.
*Filaments.*—Yellow 2A5 of irregular heights.
Pistils.
*Number.*—125–135 average.
*Stigmas.*—Normal pale orange/yellow 3A5.
*Styles.*—Pale green 1B4 at base, changing to yellow 1A5, of irregular heights. Hairy.
Receptacle:
*Color.*—29D8 deep green.
*Texture.*—Smooth, glabrous.
*Size.*—Height 8–10 mm/Width 10–12 mm.
*Shape.*—Goblet shaped.

THE DEVELOPMENT

Vegetation: Vigorous.
Blooming: Abundant and continual.
Aptitude to bearing fruits: None.
Resistance to frost: Good.
Resistance to disease: Good.

I claim:

1. A new and distinct variety of rose plant of the shrub class, characterised as to novelty by its fully double flowers of a pale creamy apricot coloring, with abundant and continual blooming and the unusual shaping of the flower being substantially as shown and described.

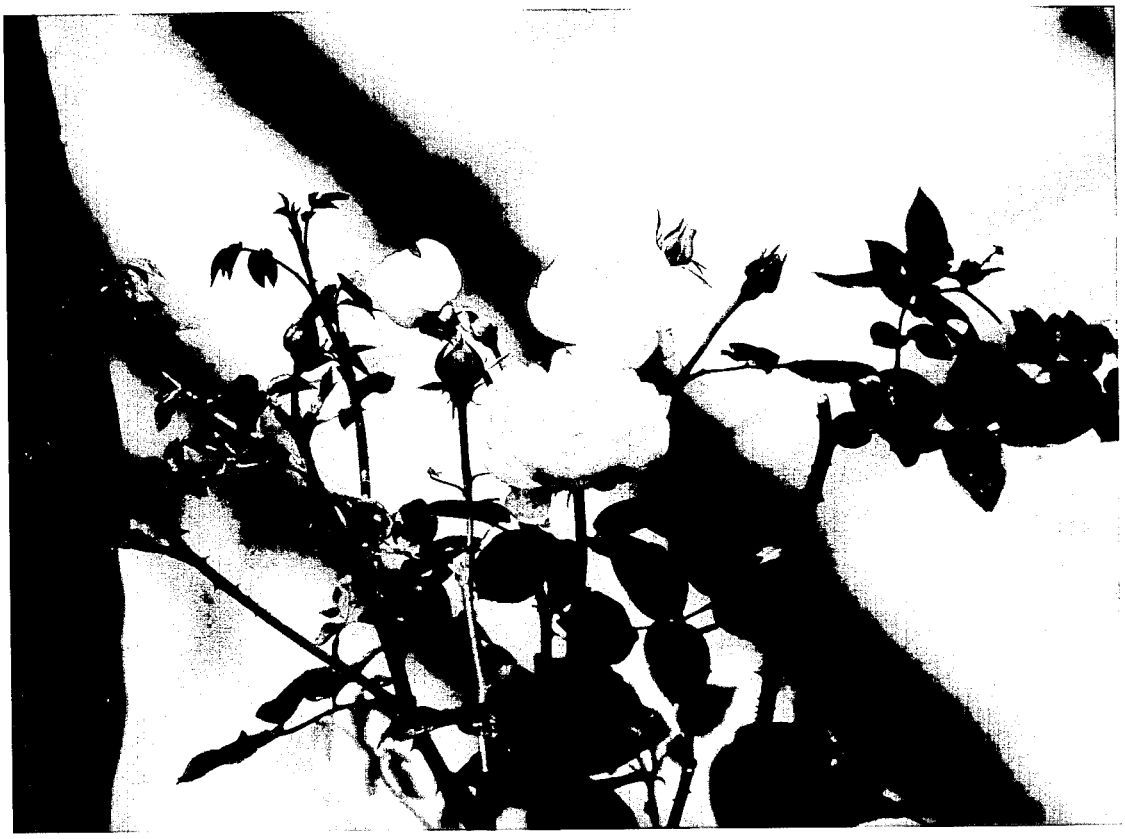

* * * * *